United States Patent
Kropf et al.

(10) Patent No.: US 10,392,579 B2
(45) Date of Patent: Aug. 27, 2019

(54) PHOTOLABILE PRO-FRAGRANCES

(71) Applicant: Henkel AG & Co. KGaA, Duesseldorf (DE)

(72) Inventors: Christian Kropf, Hilden (DE); Thomas Gerke, Duesseldorf (DE); Ursula Huchel, Cologne (DE); Axel Griesbeck, Cologne (DE); Agnieszka Landes, Bergheim (DE)

(73) Assignee: HENKEL AG & CO. KGAA, Düsseldorf (DE)

(*) Notice: Subject to any disclaimer, the term of this patent is extended or adjusted under 35 U.S.C. 154(b) by 0 days.

(21) Appl. No.: 15/771,120

(22) PCT Filed: Sep. 14, 2016

(86) PCT No.: PCT/EP2016/071689
§ 371 (c)(1),
(2) Date: Apr. 26, 2018

(87) PCT Pub. No.: WO2017/071873
PCT Pub. Date: May 4, 2017

(65) Prior Publication Data
US 2018/0305637 A1    Oct. 25, 2018

(30) Foreign Application Priority Data
Oct. 27, 2015 (DE) .......... 10 2015 220 928

(51) Int. Cl.
| | |
|---|---|
| C11B 9/00 | (2006.01) |
| C11D 3/20 | (2006.01) |
| C11D 3/50 | (2006.01) |
| C07C 69/738 | (2006.01) |
| A61K 8/37 | (2006.01) |
| A61Q 13/00 | (2006.01) |
| A61Q 19/00 | (2006.01) |
| A61L 9/01 | (2006.01) |
| A61L 2/00 | (2006.01) |

(52) U.S. Cl.
CPC .............. *C11B 9/0061* (2013.01); *A61K 8/37* (2013.01); *A61L 2/00* (2013.01); *A61L 9/01* (2013.01); *A61Q 13/00* (2013.01); *A61Q 19/00* (2013.01); *C07C 69/738* (2013.01); *C11B 9/0003* (2013.01); *C11D 3/2093* (2013.01); *C11D 3/507* (2013.01); *A61K 2800/10* (2013.01); *C07C 2601/16* (2017.05)

(58) Field of Classification Search
CPC ......... A61K 2800/10; A61K 8/37; A61L 2/00; A61L 9/01; A61Q 13/00; A61Q 19/00; C07C 2601/16; C07C 69/738; C11B 9/0003; C11B 9/0061; C11D 3/50; C11D 3/507

See application file for complete search history.

(56) References Cited

U.S. PATENT DOCUMENTS

| | | |
|---|---|---|
| 6,949,680 B2 | 9/2005 | Herrmann |
| 2011/0027208 A1 | 2/2011 | Huchel et al. |
| 2016/0347704 A1 | 12/2016 | Kropf et al. |

FOREIGN PATENT DOCUMENTS

| | | | |
|---|---|---|---|
| WO | 2009118219 A1 | 10/2009 | |
| WO | 2015124671 A1 | 8/2015 | |
| WO | WO 2015/124671 | * 8/2015 | .............. A61K 8/37 |

OTHER PUBLICATIONS

Dondi, et al, Interactions between different solar UVB/UVA filters contained in commercial suncreams and consequent loss of UV protection, Photochem. Photobiol. Sci., 5, 835-843 (2006). (Year: 2006).*
International Search Report based on application No. PCT/EP2016/071689 (5 pages + 2 pages English translation) dated Nov. 24, 2016 (for reference purpose only).
Daniele Dondi et al.; "Interactions between different solar UVB/UVA filters contained in commercial suncreams and consequent loss of UV protection"; Photochemical and Photobiological Sciences; vol. 5, No. 9; Aug. 3, 2006.

* cited by examiner

*Primary Examiner* — Erich A Leeser
(74) *Attorney, Agent, or Firm* — Viering Jentschura & Partner MBB

(57) ABSTRACT

Photolabile pro-fragrances may include the ketones of Formula (I)

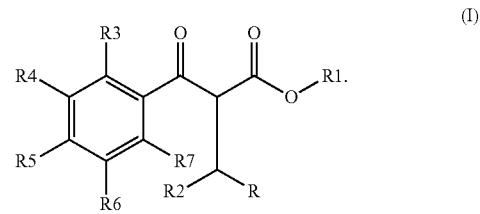

Such compounds may be used in detergents, cleaning agents, cosmetic agents, air-care agents, and combinations thereof. The photolabile pro-fragrances may create a long-lasting fragrance on surfaces or in a room using the aforementioned pro-fragrances.

7 Claims, No Drawings

PHOTOLABILE PRO-FRAGRANCES

CROSS-REFERENCE TO RELATED APPLICATION

The present application is a national stage entry according to 35 U.S.C. § 371 of PCT Application No. PCT/EP2016/071689 filed on Sep. 14, 2016, which claims priority to German Patent Application No. 10 2015 220 928.8, filed on Oct. 27, 2015; both of which are herein incorporated by reference in their entirety.

TECHNICAL FIELD

The subject matter herein generally relates to the field of pro-fragrances, as used, for example, in the field of washing or cleaning agents, cosmetic agents and air-care agents; and more specifically to ketones that function as photolabile pro-fragrances.

BACKGROUND

Washing or cleaning agents and cosmetic agents generally contain fragrances that impart a pleasant odor to the agents. The fragrances typically mask the odor of the other ingredients, thus giving the user a pleasant impression in terms of odor.

Fragrances, in particular in the field of washing agents, are important components in the composition, since it is intended for both damp laundry and dry laundry to have a fragrance that is pleasant and, where possible, fresh. A fundamental problem associated with the use of fragrances is that they are more or less highly volatile compounds, and yet a long-lasting fragrance effect is desired. In particular in the case of odorants that produce the fresh, light notes of the perfume and are particularly volatile due to their high vapor pressure, it is difficult to achieve the desired long-lasting impression of fragrance.

Fragrances can be released in a delayed manner by carrier-bound fragrance precursors, for example. A carrier-bound fragrance precursor is also referred to as a "pro-fragrance". In this connection, U.S. Pat. No. 6,949,680 discloses the use of certain phenyl or pyridyl ketones as photoactivatable substances, which in the presence of light release a terminal alkene as an active substance in a photochemical fragmentation process. This active substance has fragrance-imparting or antimicrobial activity, for example, that is initially delayed by the photochemically induced decomposition, and released on an intended surface over an extended period of time.

WO 2009/118219 A1 discloses photoactivatable substances that allow for the release of cyclic terpenes or cyclic terpenoids.

WO 2015/124671 discloses the use of certain ketones as photoactivatable substances that release an active substance in the presence of light in a photochemical fragmentation process. This active substance has fragrance-imparting activity, for example, that is initially delayed by the photochemically induced decomposition, and released on an intended surface over an extended period of time.

SUMMARY

According to a non-limiting embodiment, a compound having formula (I) is presented, i.e.

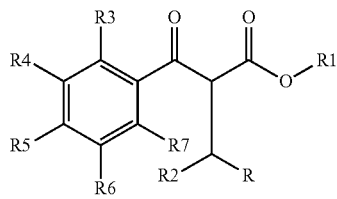

Formula (I)

where R represents a substituted hydrocarbon group, and having at least one C=O group or ester group;

where R1 represents a linear or branched alkyl group having from 6 to 20 C atoms;

where R2 represents one or more of hydrogen, a halogen atom, an aryl group, —$NO_2$, a linear or branched, substituted or unsubstituted alkoxy group having up to 15 C atoms, a linear or branched, substituted or unsubstituted alkenyl group having up to 15 C atoms, a linear or branched, substituted or unsubstituted alkyl group having up to 15 C atoms, or a substituted or unsubstituted aryl group;

where R3, R4, R5, R6 and R7 each represent, independently of one another, one or more of hydrogen, a halogen atom, an amino group, —$NO_2$, —NH alkyl, —N(alkyl)$_2$, a linear or branched, substituted or unsubstituted alkoxy group having up to 15 C atoms, a linear or branched, substituted or unsubstituted alkyl group having up to 15 C atoms, a cycloalkyl group, an acyl group, an aryl group, a —OH or —COY group, or a quaternary ammonium functional group of formula (II);

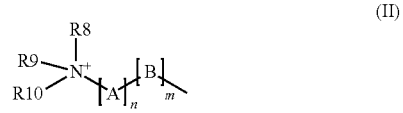

(II)

where Y represents one or more of hydrogen, alkyl, cycloalkyl, aryl, acyl, —OH, —O alkyl, —$NH_2$, —NH alkyl, —N(alkyl)$_2$ or halogen, where A represents a $CH_2$ or $CH_2CH_2O$ group, with n=1 to 20;

where B represents oxygen, with m=0 or 1, wherein m=0 if A is a $CH_2CH_2O$ group; and where R8, R9 and R10 each represent, independently of one another, one or more of H or a substituted or unsubstituted group containing alkyl, cycloalkyl, alkenyl, aryl or acyl groups, and wherein in each case two of the groups R8, R9 and R10 can be interconnected by a ring connection.

According to yet another non-limiting embodiment of a method, a method may include applying at least one compound of Formula (I) to at least one surface to be fragranced, and then exposing the surface(s) to light.

DETAILED DESCRIPTION

The photoactivatable substances, e.g. pro-fragrances, allow odorant ketones, in particular damascones, to be released in a delayed manner.

This object is solved by a compound of general formula (I),

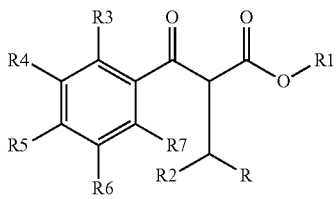

Formula (I)

wherein, in this formula (I),

R represents an optionally substituted hydrocarbon group having preferably from 2 to 20 C atoms, and having at least one C=O group or ester group, preferably a C=O group;
R1 represents a linear or branched alkyl group having from 6 to 20 C atoms;
R2 represents hydrogen, a halogen atom, an aryl group, —$NO_2$, a linear or branched, substituted or unsubstituted alkoxy group having up to 15 C atoms, a linear or branched, substituted or unsubstituted alkenyl group having up to 15 C atoms, a linear or branched, substituted or unsubstituted alkyl group having up to 15 C atoms or a substituted or unsubstituted aryl group;
R3, R4, R5, R6 and R7 each represent, independently of one another, hydrogen, a halogen atom, an amino group, —$NO_2$, —NH alkyl, —N(alkyl)$_2$, a linear or branched, substituted or unsubstituted alkoxy group having up to 15 C atoms, a linear or branched, substituted or unsubstituted alkyl group having up to 15 C atoms, a cycloalkyl group, an acyl group, an aryl group, a —OH or —COY group, or a quaternary ammonium group of formula (II);

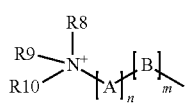
(II)

Y represents hydrogen, alkyl, cycloalkyl, aryl, acyl, —OH, —O alkyl, —$NH_2$, —NH alkyl, —N(alkyl)$_2$ or halogen,
A represents a $CH_2$ or $CH_2CH_2O$ group, with n=1 to 20;
B represents oxygen, with m=0 or 1, where m=0 if A is a $CH_2CH_2O$ group; and
R8, R9 and R10 each represent, independently of one another, H or a substituted or unsubstituted group containing alkyl, cycloalkyl, alkenyl, aryl or acyl groups, and it being possible in each case for two of the groups R8, R9 and R10 to be interconnected by a ring connection.

Within the meaning of the present disclosure, —COY groups are to be understood to be carbonyl compounds of general formula —(C=O)—Y, wherein the group —Y is defined as described above.

It was surprisingly found that the pro-fragrances are particularly effective at allowing odorant ketones, in particular damascones, to be released in a delayed manner, while at the same time providing a higher fragrance intensity than that in photocages known from the prior art. The use of the pro-fragrances in washing, cleaning or care agents therefore results in an improved long-lasting fragrance effect when said agents are used, in particular in the context of treating textiles. For example, when the pro-fragrances are used in a laundry treatment agent, such as a washing agent or softener, it has been found that an improved long-lasting fragrance effect for the treated laundry is achieved. Furthermore, corresponding products have a particularly high level of storage stability. The agents also allow the total amount of perfume contained in the agent to be reduced, while still achieving fragrance benefits on the laundered textiles, in particular with regard to the feeling of freshness.

The pro-fragrance of general formula (I) is a suitable pro-fragrance for all typical fragrance ketones, in particular selected from Buccoxime, iso-jasmone, methyl beta-naphthyl ketone, musk indanone, tonalide/musk plus, alpha-damascone, beta-damascone, delta-damascone, gamma-damascone, damascenone, damask rose, methyl dihydrojasmonate, menthone, carvone, camphor, fenchone, alpha-ionone, beta-ionone, gamma-methyl ionone, referred to as ionone, fleuramone, dihydrojasmone, cis-jasmone, 1-(1,2,3,4,5,6,7,8-octahydro-2,3,8,8-tetramethyl-2-naphthyl)ethan-1-one (Iso E Super®), methyl cedrenyl ketone or methyl cedrylone, acetophenone, methylacetophenone, para-methoxyacetophenone, methyl-beta-naphtyl ketone, benzyl acetone, benzophenone, para-hydroxyphenyl butanone, 3-methyl-5-propyl-2-cyclohexen-1-one (celery ketone or livescone), 6-isopropyldecahydro-2-naphtone, dimethyl octenone, frescomenthe, 4-(1-ethoxyvinyl)-3,3,5, 5-tetramethylcyclohexanone, methyl heptenone, 2-(2-(4-methyl-3-cyclohexene-1-yl)propyl)cyclopentanone, 1-(p-menthene-6(2)yl)-1-propanone, 4-(4-hydroxy-3-methoxyphenyl)-2-butanone, 2-acetyl-3,3-dimethyl-norbornane, 6,7-dihydro-1,1,2,3,3-pentamethyl-4(5H)-indanone, 4-damascol, dulcinyl or cassione, gelsone, hexalone, isocyclemone E, methyl cyclocitrone, methyl lavender ketone, orivone, para-tertiary butylcyclohexanone, verdone, delphone, muscone, neobutenone, plicatone, veloutone, 2,4,4,7-tetramethyl-oct-6-en-3-one, tetrameran or mixtures thereof. Preferably, the ketones may be selected from damascones, carvone, gamma-methyl ionone, Iso E Super®, 2,4,4,7-tetramethyl-oct-6-en-3-one, benzyl acetone, damascenone, methyl dihydrojasmonate, methyl cedrylone, hedione and mixtures thereof. The ketones are most preferably selected from all damascones and damascenones.

The above-mentioned fragrances can be bound to the compound of formula (I) as group R. The stored ketones can be released upon exposure to light having a wavelength of from 200 to 600 nm.

According to various preferred embodiments, the substituent R in formula (I) represents a hydrocarbon group having from 2 to 20 carbon atoms, and having at least one carbonyl group or ester group. The hydrocarbon group may have, in addition to the at least one carbonyl or ester group, additional substituents. In particular, the hydrocarbon group is a fragrance ketone group which is bound by the carbon atom of a methylene group in the alpha position in relation to the carbonyl carbon atom. In this case, the fragrance ketone may be selected from the above-mentioned ketones.

According to a preferred embodiment, the substituent R1 in formula (I) represents a linear or branched alkyl group having from 6 to 16 C atoms, such as n-hexyl, n-heptyl, n-octyl, 2-ethylhexyl, isooctyl (2,2,4-trimethylpentyl), n-nonyl, n-decyl, 3-propylheptyl, n-undecyl, n-dodecyl, n-tridecyl, n-tetradecyl, n-pentadecyl or n-hexadecyl, preferably a linear, unsubstituted alkyl group having 10, 11, 12, 13, 14, 15 or 16 C atoms, for example n-decyl, n-undecyl, n-dodecyl, n-tridecyl, n-tetradecyl, n-pentadecyl or n-hexadecyl, very particularly preferably decyl, dodecyl, tetradecyl or hexadecyl. In various embodiments, R1 in formula (I) is not a C16 or C20 alkyl.

According to a further preferred embodiment, the substituent R2 in formula (I) represents a linear or branched, substituted or unsubstituted alkyl group having from 1 to 6 C atoms, preferably from 1 to 3 C atoms, in particular a methyl group.

According to yet another preferred embodiment, the substituents R3, R4, R5, R6 and R7 in formula (I) represent, independently of one another, hydrogen or a linear or branched, substituted or unsubstituted alkoxy group having up to 6 C atoms or a linear or branched, substituted or unsubstituted alkyl group having up to 6 C atoms, preferably hydrogen.

In various embodiments, in the definition of Y and in the —O alkyl, —NH alkyl and —N(alkyl)$_2$ groups, "alkyl" stands for a linear or branched, substituted or unsubstituted alkyl group, having preferably up to 15 C atoms. "Cycloalkyl" stands for corresponding cyclic alkyl groups, having preferably from 3 to 15 C atoms. "Aryl" preferably stands for a substituted or unsubstituted aryl group, wherein aryl group may also comprise from 1 to 6 heteroatoms, such as N, O or S, as ring atoms and to thus form a heteroaryl group, preferably a C6-C14 aryl. In particular, the term also comprises 5-membered heteroaryl groups that cannot be derived directly by replacing a ring C atom with a heteroatom of an aryl group, such as furan, thiofuran or pyrrole groups. "Acyl" preferably stands for a —C(O) alkyl, where "alkyl" is defined as above.

"Substituted", as used herein with reference to alkyl, alkenyl, alkoxy and acyl groups, means that the corresponding group has one or more substituents that replace one or more hydrogen atoms and are selected from —OR', —NR'R", —SR', —C(O)R', —C(O)OR', —C(O)NR'R", —NR'—C(O)—R" and halogen, wherein R' and R" represent hydrogen or an unsubstituted C1-10 alkyl.

"Substituted", as used herein with reference to cycloalkyl, aryl or other cyclic hydrocarbon groups, means that the corresponding group has one or more substituents that replace one or more hydrogen atoms and are selected from —OR', —NR'R", —SR', —C(O)R', —C(O)OR', —C(O)NR'R", —NR'—C(O)—R", halogen, and C1-10 alkyl, =CR'R", or C2-10 alkenyl, wherein R' and R" represent hydrogen or an unsubstituted C1-10 alkyl.

In various embodiments, unless indicated otherwise, the alkyl, aryl, acyl and alkenyl groups or radicals contain up to 20, preferably up to 12, carbon atoms.

According to a preferred embodiment, pro-fragrances corresponding to the following formula (III) are particularly preferred:

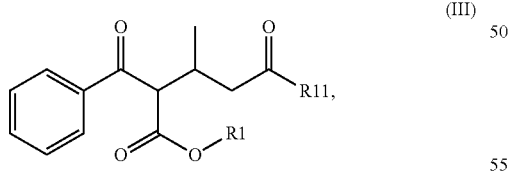

(III)

wherein
R1 is defined as above and preferably represents a linear or branched, substituted or unsubstituted alkyl group having from 6 to 16 C atoms, such as n-hexyl, n-heptyl, n-octyl, 2-ethylhexyl, isooctyl (2,2,4-trimethylpentyl), n-nonyl, n-decyl, 3-propylheptyl, n-undecyl, n-dodecyl, n-tridecyl, n-tetradecyl, n-pentadecyl or n-hexadecyl, more preferably a linear, unsubstituted alkyl group having from 10 to 16 C atoms, for example n-decyl, n-undecyl, n-dodecyl, n-tridecyl, n-tetradecyl, n-pentadecyl or n-hexadecyl, very particularly preferably decyl, dodecyl, tetradecyl or hexadecyl; and R11 represents a hydrocarbon group having at least 5 C atoms, and having in particular a cyclic, optionally substituted hydrocarbon group, preferably a cyclic, substituted alkenyl group, in particular

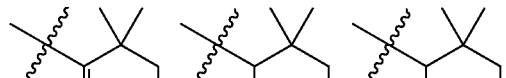

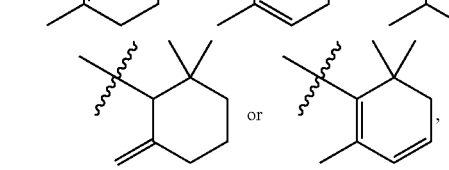

preferably

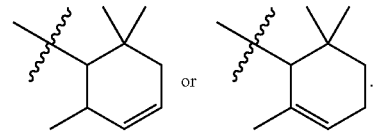

According to a further embodiment, pro-fragrances corresponding to the following formulae (IV) to (XI) are particularly preferred:

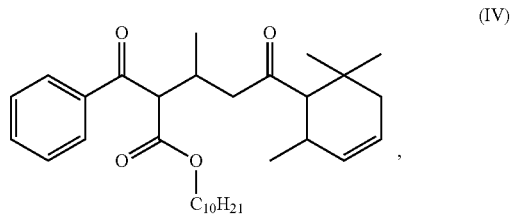

(IV)

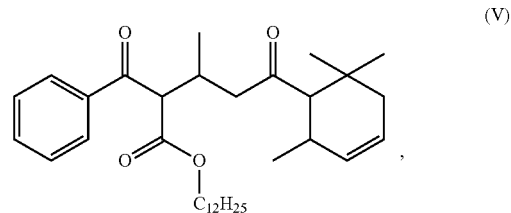

(V)

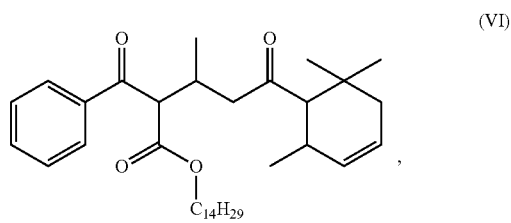

(VI)

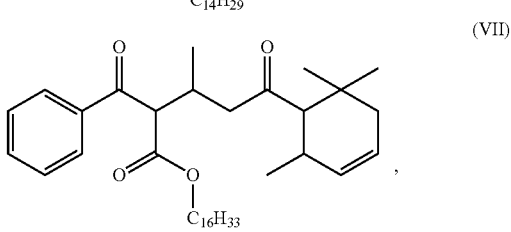

(VII)

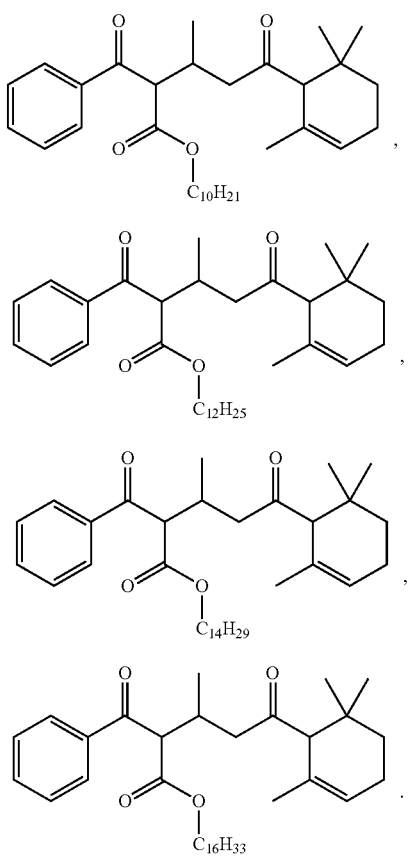

The pro-fragrances may be stably incorporated into typical washing or cleaning agent matrices, cosmetics, and existing odorant compositions. They allow the stored fragrances to be released in a delayed manner, said fragrances being, inter alia, alpha-damascone, beta-damascone, gamma-damascone or delta-damascone, or damascenones, in particular delta-damascenone. These fragrances impart a particularly long-lasting impression of freshness to typical washing or cleaning agents and cosmetics. In particular the dried, washed textile benefits from the good fragrance effect of long-term freshness. The stored odorant is released slowly upon exposure to light (electromagnetic radiation) having a wavelength of from 200 to 600 nm, as shown in a simplified manner by the following reaction equation given by way of example:

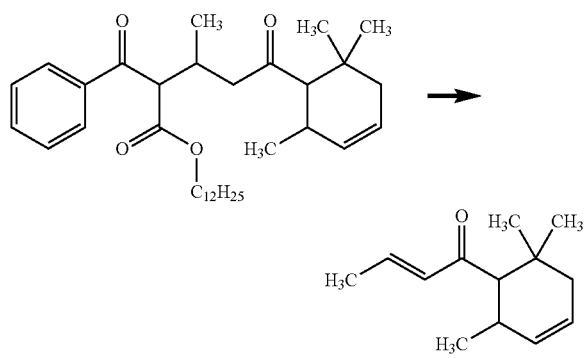

A further non-limiting embodiment relates to a a washing or cleaning agent, preferably a washing agent, softener or auxiliary washing agent, containing at least one pro-fragrance, the pro-fragrance preferably being contained in a total amount of between 0.0001 and 5 wt. %, advantageously between 0.001 and 4 wt. %, more advantageously between 0.01 and 3 wt. %, in particular between 0.1 and 2 wt. %, in each case based on the overall agent. Suitable cleaning agents are, for example, cleaning agents for hard surfaces, such as preferably dishwasher detergents. The cleaning agents may also be cleaning agents such as household cleaners, all-purpose cleaners, window cleaners, floor cleaners, etc. Preferably, the cleaning agent may be a product for cleaning toilet bowls and urinals, advantageously a flush cleaner for being hung in the toilet bowl.

According to a preferred embodiment, the washing or cleaning agent contains at least one surfactant selected from anionic, cationic, nonionic, zwitterionic and amphoteric surfactants or mixtures thereof.

According to a further preferred embodiment, the agent is present in solid or liquid form.

Within the meaning of the present embodiments, unless indicated otherwise, stated amounts in wt. % for the agent refer to the total weight of the agent.

A further non-limiting embodiment relates to a cosmetic agent, containing at least one pro-fragrance, which agent preferably contains the pro-fragrance in a total amount of between 0.0001 and 5 wt. %, advantageously between 0.001 and 4 wt. %, more advantageously between 0.01 and 3 wt. %, in particular between 0.1 and 2 wt. %, in each case based on the overall agent.

A further non-limiting embodiment relates to an air-care agent (e.g. room air freshener, room deodorizer, room spay, etc.), containing at least one pro-fragrance, said pro-fragrance preferably being contained in a total amount of between 0.0001 and 50 wt. %, advantageously between 0.001 and 5 wt. %, more advantageously between 0.01 and 3 wt. %, in particular between 0.1 and 2 wt. %, in each case based on the overall agent.

According to a further preferred embodiment, additional fragrances and/or pro-fragrances are contained in an agent (i.e. a washing or cleaning agent, cosmetic agent or air-care agent), said additional fragrances being in particular selected from the group comprising fragrances of natural or synthetic origin, preferably more volatile fragrances, higher-boiling fragrances, solid fragrances and/or adherent fragrances.

Examples of adherent odorants are essential oils such as angelica root oil, anise oil, arnica blossom oil, basil oil, bay oil, bergamot oil, champaca blossom oil, noble fir alba oil, noble fir alba cone oil, elemi oil, eucalyptus oil, fennel oil, spruce needle oil, galbanum oil, geranium oil, ginger grass oil, guaiac wood oil, gurjun balsam oil, helichrysum oil, ho oil, ginger oil, iris oil, cajuput oil, calamus oil, chamomile oil, camphor oil, cananga oil, cardamom oil, cassia oil, pine needle oil, copaiba balsam oil, coriander oil, spearmint oil, caraway oil, cumin oil, lavender oil, lemongrass oil, lime oil, mandarin oil, melissa oil, musk seed oil, myrrh oil, clove oil, neroli oil, niaouli oil, olibanum oil, orange oil, oregano oil, palmarosa oil, patchouli oil, Peru balsam oil, petitgrain oil, pepper oil, peppermint oil, allspice oil, pine oil, rose oil, rosemary oil, sandalwood oil, celery oil, spike lavender oil, star anise oil, turpentine oil, thuja oil, thyme oil, verbena oil, vetiver oil, juniper berry oil, wormwood oil, wintergreen oil, ylang-ylang oil, hyssop oil, cinnamon oil, cinnamon leaf oil, citronella oil, lemon oil, and cypress oil.

However, higher-boiling and solid odorants of natural or synthetic origin may also be used as adherent odorants or odorant mixtures, i.e. fragrances. These compounds include the compounds indicated in the following and mixtures thereof: ambrettolide, alpha-amylcinnamaldehyde, anethole, anisaldehyde, anise alcohol, anisole, anthranilic acid methyl ester, acetophenone, benzylacetone, benzaldehyde, benzoic acid ethyl ester, benzophenone, benzyl alcohol, benzyl acetate, benzyl benzoate, benzyl formate, benzyl valerianate, borneol, bornyl acetate, alpha-bromostyrene, n-decyl aldehyde, n-dodecyl aldehyde, eugenol, eugenol methyl ether, eucalyptol, farnesol, fenchone, fenchyl acetate, geranyl acetate, geranyl formate, heliotropin, heptyne carboxylic acid methyl ester, heptaldehyde, hydroquinone dimethyl ether, hydroxycinnamaldehyde, hydroxycinnamyl alcohol, indole, irone, isoeugenol, isoeugenol methyl ether, isosafrole, jasmone, camphor, carvacrol, carvone, p-cresol methyl ether, coumarin, p-methoxyacetophenone, methyl n-amyl ketone, methylanthranilic acid methyl ester, p-methylacetophenone, methylchavicol, p-methylquinoline, methyl beta-naphthyl ketone, methyl n-nonyl acetaldehyde, methyl n-nonyl ketone, muscone, beta-naphthol ethyl ether, beta-naphthol methyl ether, nerol, nitrobenzene, n-nonyl aldehyde, nonyl alcohol, n-octylaldehyde, p-oxyacetophenone, pentadecanolide, beta-phenethyl alcohol, phenylacetaldehyde dimethyl acetal, phenylacetic acid, pulegone, safrole, salicylic acid isoamyl ester, salicylic acid methyl ester, salicylic acid hexyl ester, salicylic acid cyclohexyl ester, santalol, skatole, terpineol, thymene, thymol, gamma-undecalactone, vanillin, veratraldehyde, cinnamaldehyde, cinnamyl alcohol, cinnamic acid, cinnamic acid ethyl ester, cinnamic acid benzyl ester. More volatile fragrances include in particular lower-boiling odorants of natural or synthetic origin, which may be used alone or in mixtures. Examples of more volatile fragrances are alkyl isothiocyanates (alkyl mustard oils), butanedione, limonene, linalool, linayl acetate and propionate, menthol, menthone, methyl-n-heptenone, phellandrene, phenylacetaldehyde, terpinyl acetate, citral and citronellal.

According to a further preferred embodiment, the agent (i.e. a washing or cleaning agent, cosmetic agent or air-care agent) has at least one, preferably a plurality of, active components, in particular washing, care, cleansing and/or cosmetic components, advantageously selected from the group comprising anionic surfactants, cationic surfactants, amphoteric surfactants, nonionic surfactants, acidifying agents, alkalizing agents, anti-crease compounds, antibacterial substances, antioxidants, anti-redeposition agents, antistatic agents, builders, bleaching agents, bleach activators, bleach stabilizers, bleach catalysts, ironing aids, cobuilders, shrinkage preventers, electrolytes, enzymes, color protectants, colorants, dyes, dye transfer inhibitors, fluorescing agents, fungicides, germicides, odor-complexing substances, adjuvants, hydrotropes, rinse aids, complexing agents, preservatives, corrosion inhibitors, water-miscible organic solvents, optical brighteners, perfume carriers, luster agents, pH adjusters, proofing and impregnation agents, polymers, anti-swelling and anti-slip agents, foam inhibitors, phyllosilicates, soil-repellent substances, silver protectants, silicone oils, soil-release active ingredients, UV protection substances, viscosity regulators, thickeners, discoloration inhibitors, graying inhibitors, vitamins and/or softeners.

The amounts of the individual ingredients in the agents (i.e. washing or cleaning agents, cosmetic agents or air-care agents) in each case depend on the intended purpose of the agents in question, and a person skilled in the art is in principle familiar with the ranges of the amounts of ingredients that should be used, or may obtain these from the relevant technical literature. Depending on the intended purpose of the agents, the surfactant content, for example, is selected to be higher or lower. The surfactant content of washing agents, for example, may typically be, for example, between 10 and 50 wt. %, preferably between 12.5 and 30 wt. %, and in particular between 15 and 25 wt. %, while, for example, cleaning agents for automatic dishwashing may contain, for example, between 0.1 and 10 wt. %, preferably between 0.5 and 7.5 wt. %, and in particular between 1 and 5 wt. %, of surfactants.

The agents (i.e. washing or cleaning agents, cosmetic agents or air-care agents) may contain surfactants, preferably anionic surfactants, nonionic surfactants and mixtures thereof, but also cationic surfactants. Suitable nonionic surfactants are in particular ethoxylation and/or propoxylation products of alkyl glycosides and/or linear or branched alcohols each having from 12 to 18 C atoms in the alkyl portion and from 3 to 20, preferably from 4 to 10, alkyl ether groups. Also usable are corresponding ethoxylation and/or propoxylation products of N-alkylamines, vicinal diols, fatty acid esters, and fatty acid amides which, with regard to the alkyl portion, correspond to the stated long-chain alcohol derivatives, and of alkylphenols having from 5 to 12 C atoms in the alkyl group.

Suitable anionic surfactants are in particular soaps and those containing sulfate or sulfonate groups having preferably alkali ions as cations. Usable soaps are preferably the alkali salts of saturated or unsaturated fatty acids having from 12 to 18 C atoms. Fatty acids of this kind may also be used in a not completely neutralized form. Usable sulfate-type surfactants include the salts of sulfuric acid semiesters of fatty alcohols having from 12 to 18 C atoms and the sulfation products of the stated nonionic surfactants having a low degree of ethoxylation. Usable sulfonate-type surfactants include linear alkylbenzenesulfonates having from 9 to 14 C atoms in the alkyl portion, alkanesulfonates having from 12 to 18 C atoms, and olefin sulfonates having from 12 to 18 C atoms, resulting from the reaction of corresponding monoolefins with sulfur trioxide, and alpha-sulfo fatty acid esters, resulting from the sulfonation of fatty acid methyl or ethyl esters.

Cationic surfactants are preferably selected from among esterquats and/or quaternary ammonium compounds (QACs) according to general formula $(R^{I})(R^{II})(R^{III})(R^{IV})N^{+}X^{-}$, in which $R^{I}$ to $R^{IV}$ represent $C_{1-22}$ alkyl groups, $C_{7-28}$ arylalkyl groups or heterocyclic groups that are the same or different, wherein two groups, or, in the case of aromatic bonding such as in pyridine, even three groups form, together with the nitrogen atom, the heterocycle, for example a pyridinium or imidazolinium compound, and $X^{-}$ represents halide ions, sulfate ions, hydroxide ions, or similar anions. QACs may be prepared by reacting tertiary amines with alkalizing agents, for example methyl chloride, benzyl chloride, dimethyl sulfate, dodecyl bromide, but also ethylene oxide. The alkylation of tertiary amines with a long alkyl group and two methyl groups is particularly simple; the quaternization of tertiary amines with two long groups and a methyl group may also be carried out under mild conditions using methyl chloride. Amines having three long alkyl groups or hydroxy-substituted alkyl groups are less reactive, and are quaternized using dimethyl sulfate, for example. Examples of suitable QACs are benzalkonium chloride (N-alkyl-N,N-dimethylbenzyl ammonium chloride), Benzalkon B (m,p-dichlorobenzyldimethyl-$C_{12}$ alkylammonium chloride, benzoxonium chloride (benzyldodecyl-bis-(2-hydroxyethyl) ammonium chloride), cetrimonium bromide (N-hexadecyl-N,N-trimethylammonium bromide), benzethonium chloride (N,N-dimethyl-N-[2-[2-[p-(1,1,3,3-tetramethylbutyl)phenoxy]ethoxy]ethyl] benzylammonium chloride), dialkyldimethylammonium chlorides such as di-n-decyldimethyl ammonium chloride, didecyldimethyl ammonium bromide, dioctyldimethyl ammonium chloride, 1-cetylpyridinium chloride, and thiazoline iodide, and mixtures thereof. Preferred QACs are benzalkonium chlorides having $C_8$-$C_{22}$ alkyl groups, in particular $C_{12}$-$C_{14}$ alkylbenzyldimethyl ammonium chloride.

Preferred esterquats are methyl-N-(2-hydroxyethyl)-N,N-di(talgacyloxyethyl) ammonium methosulfate, bis-(palmitoyl)ethylhydroxyethylmethyl ammonium methosulfate or methyl-N,N-bis(acyloxyethyl)-N-(2-hydroxyethyl) ammonium methosulfate. Commercially available examples are the methylhydroxyalkyldialkoyloxyalkyl ammonium methosulfates marketed by Stepan under the trademark Stepantex®, the products from BASF SE known under the trade name Dehyquart®, or the products from the manufacturer Evonik known under the name Rewoquat®.

Surfactants are contained in the agents (i.e. washing or cleaning agents, cosmetic agents or air-care agents) in amount proportions of preferably from 5 wt. % to 50 wt. %, in particular from 8 wt. % to 30 wt. %. Preferably up to 30 wt. %, in particular from 5 wt. % to 15 wt. %, surfactants, preferably including cationic surfactants at least in part, are used in particular in laundry aftertreatment agents.

An agent, in particular a washing or cleaning agent, preferably contains at least one water-soluble and/or water-insoluble, organic and/or inorganic builder. The water-soluble organic builders include polycarboxylic acids, in particular citric acid and saccharic acid acids, monomeric and polymeric aminopolycarboxylic acids, in particular methylglycinediacetic acid, nitrilotriacetic acid, and ethylenediaminetetraacetic acid as well as polyaspartic acid, polyphosphonic acids, in particular amino tris(methylenephosphonic acid), ethylenediamine tetrakis(methylenephosphonic acid), and 1-hydroxyethane-1,1-diphosphonic acid, polymeric hydroxy compounds such as dextrin, and polymeric (poly)carboxylic acids, polymeric acrylic acids, methacrylic acids, maleic acids, and mixed polymers thereof, which may also contain small portions of polymerizable substances, without a carboxylic acid functionality, in the polymer. Compounds of this class which are suitable, although less preferred, are copolymers of acrylic acid or methacrylic acid with vinyl ethers, such as vinyl methyl ethers, vinyl esters, ethylene, propylene, and styrene, in which the proportion of the acid is at least 50 wt. %. The organic builders may, in particular for the production of liquid agents, be used in the form of aqueous solutions, preferably in the form of 30 to 50 wt. % aqueous solutions. All indicated acids are generally used in the form of water-soluble salts thereof, in particular alkali salts thereof.

Organic builders may, if desired, be contained in amounts of up to 40 wt. %, in particular up to 25 wt. %, and preferably from 1 wt. % to 8 wt. %. Amounts close to the stated upper limit are preferably used in paste-form or liquid, in particular water-containing, agents. Laundry aftertreatment agents, such as softeners, may optionally also be free of organic builder.

In particular alkali silicates and polyphosphates, preferably sodium triphosphate, are suitable as water-soluble inorganic builder materials. In particular crystalline or amorphous alkali aluminosilicates may, if desired, be used in amounts of up to 50 wt. %, preferably no more than 40 wt. %, and, in liquid agents, in particular from 1 wt. % to 5 wt. %, as water-insoluble, water-dispersible inorganic builder materials. Among these, crystalline sodium aluminosilicates of washing agent quality, in particular zeolite A, P and optionally X, are preferred. Amounts close to the stated upper limit are preferably used in solid particulate agents. Suitable aluminosilicates have in particular no particles having a particle size greater than 30 m and preferably comprise at least 80 wt. % of particles having a size smaller than 10 m. Suitable substitutes or partial substitutes for the stated aluminosilicate are crystalline alkali silicates, which may be present alone or in a mixture with amorphous silicates. The alkali silicates that are usable in the agents as builders preferably have a molar ratio of alkali oxide to $SiO_2$ of less than 0.95, in particular from 1:1.1 to 1:12, and may be present in amorphous or crystalline form. Preferred alkali silicates are sodium silicates, in particular amorphous sodium silicates having a $Na_2O:SiO_2$ molar ratio of from 1:2 to 1:2.8. Preferably used as crystalline silicates, which may be present alone or in a mixture with amorphous silicates, are crystalline phyllosilicates of general formula $Na_2Si_xO_{2x+1} \cdot yH_2O$, where x, referred to as the module, is a number from 1.9 to 4, y is a number from 0 to 20, and preferred values for x are 2, 3 or 4. Preferred crystalline phyllosilicates are those in which x in the stated general formula attains the values 2 or 3. In particular, both beta-sodium and delta-sodium disilicates ($Na_2Si_2O_5 \cdot yH_2O$) are preferred. Practically water-free crystalline alkali silicates of the above general formula, in which x is a number from 1.9 to 2.1 and which are produced from amorphous alkali silicates, may also be used in agents. In a further preferred embodiment of agents, a crystalline sodium phyllosilicate having a module of from 2 to 3, as can be produced from sand and soda, is used. Crystalline sodium silicates having a module in the range of from 1.9 to 3.5 are used in a further preferred embodiment of agents. If alkali aluminosilicate, in particular zeolite, is also present as an additional builder, the weight ratio of aluminosilicate to silicate, in each case based on water-free active substances, is preferably from 1:10 to 10:1. In agents containing both amorphous and crystalline alkali silicates, the weight ratio of amorphous alkali silicate to crystalline alkali silicate is preferably from 1:2 to 2:1 and in particular from 1:1 to 2:1.

Builders are, if desired, preferably contained in the agents in amounts of up to 60 wt. %, in particular from 5 wt. % to 40 wt. %. Laundry aftertreatment agents, for example softeners, are preferably free of inorganic builders.

In particular, organic peracids or peracid salts of organic acids, such as phthalimidopercapronic acid, perbenzoic acid or salts of diperdodecandioic acid, hydrogen peroxide, and inorganic salts that release hydrogen peroxide under the use conditions, such as perborate, percarbonate, and/or persilicate, are suitable as peroxygen compounds. If solid peroxygen compounds are intended to be used, these may be used in the form of powders or granules, which may also be coated in a manner known in principle. The optional use of alkali percarbonate, alkali perborate monohydrate or, in particular in liquid agents, hydrogen peroxide in the form of aqueous solutions containing from 3 wt. % to 10 wt. % hydrogen peroxide, is particularly preferred. If an agent contains bleaching agents, such as preferably peroxygen compounds, these are present in amounts of preferably up to 50 wt. %, in particular from 5 wt. % to 30 wt. %. The addition of small amounts of known bleaching agent stabilizers such as phosphonates, borates or metaborates, metasilicates and magnesium salts such as magnesium sulfate, may be expedient.

Compounds which, under perhydrolysis conditions, result in aliphatic peroxocarboxylic acids having preferably from 1 to 10 C atoms, in particular from 2 to 4 C atoms, and/or optionally substituted perbenzoic acid, may be used as bleach activators. Substances that have O acyl and/or N acyl groups of the stated number of C atoms and/or optionally substituted benzoyl groups are suitable. Preferred are polyacylated alkylene diamines, in particular tetraacetylethylenediamine (TAED), acylated triazine derivatives, in particular 1,5-diacetyl-2,4-dioxohexahydro-1,3,5-triazine (DADHT), acylated glycolurils, in particular tetraacetylglycoluril (TAGU), N-acylimides, in particular N-nonanoyl succinimide (NOSI), acylated phenolsulfonates, in particular n-nonanoyl- or isononanoyloxybenzenesulfonate (n- or iso-NOBS), carboxylic acid anhydrides, in particular phthalic acid anhydride, acylated polyhydric alcohols, in particular triacetin, ethylene glycol diacetate, 2,5-diacetoxy-2,5-dihydrofuran and enol ester, and acetylated sorbitol and mannitol or mixtures thereof (SORMAN), acylated sugar derivatives, in particular pentaacetyl glucose (PAG), pentaacetyl fructose, tetraacetyl xylose and octaacetyl lactose, and acetylated, optionally N-alkylated glucamine and gluconolactone, and/or N-acylated lactams, for example N-benzoylcaprolactam. Hydrophilically substituted acyl acetals and acyl lactams are likewise preferably used. Combinations of conventional bleach activators may also be used. Bleach activators of this kind may be contained in a typical amount range, preferably in amounts of from 1 wt. % to 10 wt. %, in particular from 2 wt. % to 8 wt. %, based on the overall agent.

In addition to or instead of the conventional bleach activators listed above, sulfonimines and/or bleach-enhancing transition metal salts or transition metal complexes may also be contained as what are referred to as bleach catalysts.

Suitable as enzymes that can be used in the agents are those from the class of proteases, cutinases, amylases, pullulanases, hemicellulases, cellulases, lipases, oxidases, and peroxidases, and mixtures thereof. Enzymatic active ingredients obtained from fungi or bacteria, such as *Bacillus subtilis*, *Bacillus licheniformis*, *Streptomyces griseus*, *Humicola lanuginosa*, *Humicola insolens*, *Pseudomonas pseudoalcaligenes* or *Pseudomonas cepacia* are particularly suitable. The optionally used enzymes may be adsorbed on carrier substances and/or embedded in coating substances to protect the enzymes from premature inactivation. The enzymes are, if desired, preferably contained in the agents in amounts no greater than 5 wt. %, in particular from 0.2 wt. % to 2 wt. %.

The agents may optionally contain, for example, derivatives of diaminostilbene disulfonic acid or alkali metal salts thereof as optical brighteners. Suitable are, for example, salts of 4,4'-bis(2-anilino-4-morpholino-1,3,5-triazinyl-6-amino)stilbene-2,2'-disulfonic acid or compounds having a similar structure which, instead of the morpholino group, have a diethanolamino group, a methylamino group, an anilino group or a 2-methoxyethylamino group.

Suitable foam inhibitors include, for example, organopolysiloxanes and mixtures thereof with microfine, optionally silanated silicic acid and paraffin waxes and mixtures thereof with silanated silicic acid or bis-fatty acid alkylene diamides. Mixtures of various foam inhibitors are also advantageously used, for example those made up of silicones, paraffins, or waxes. The foam inhibitors, in particular silicone-containing and/or paraffin-containing foam inhibitors, are preferably bound to a granular carrier substance that is soluble or dispersible in water. Mixtures of paraffin waxes and bistearylethylenediamides are particularly preferred.

Furthermore, the agents may also contain components that positively influence the capability for washing out oil and grease from textiles, or what are referred to as soil-release active ingredients. This effect is particularly apparent when a textile is soiled which has been previously washed several times using an agent that contains this deoiling and degreasing component. Preferred deoiling and degreasing components include, for example, nonionic cellulose ethers such as methylcellulose and methylhydroxypropylcellulose having a proportion of from 15 to 30 wt. % of methoxyl groups and from 1 to 15 wt. % of hydroxypropoxyl groups, in each case based on the nonionic cellulose ether, and the polymers of phthalic acid and/or terephthalic acid known from the prior art, or derivatives thereof, with monomeric and/or polymeric diols, in particular polymers of ethylene terephthalates and/or polyethylene glycol terephthalates or anionically and/or nonionically modified derivatives thereof.

The agents may also contain dye transfer inhibitors, preferably in amounts of from 0.1 wt. % to 2 wt. %, in particular from 0.1 wt. % to 1 wt. %, which, in a preferred embodiment, are polymers of vinylpyrrolidone, vinyl imidazole or vinyl pyridine-N-oxide, or copolymers thereof.

The function of graying inhibitors is to keep the dirt that is removed from the textile fiber suspended in the liquor. Water-soluble colloids, which are usually organic, are suitable for this purpose, for example starch, sizing material, gelatine, salts of ethercarboxylic acids or ethersulfonic acids of starch or of cellulose, or salts of acidic sulfuric acid esters of cellulose or of starch. Water-soluble polyamides containing acidic groups are also suitable for this purpose. Starch derivatives other than those mentioned above may also be used, for example aldehyde starches. Cellulose ethers, such as carboxymethylcellulose (Na salt), methylcellulose, hydroxyalkylcellulose, and mixed ethers, such as methylhydroxyethylcellulose, methylhydroxypropyl cellulose, methylcarboxymethylcellulose and mixtures thereof, may preferably be used, for example, in amounts of from 0.1 to 5 wt. %, based on the agents.

The organic solvents that are usable in the agents, in particular when the agents are present in liquid or paste-like form, include alcohols having from 1 to 4 C atoms, in particular methanol, ethanol, isopropanol, and tert-butanol, diols having from 2 to 4 C atoms, in particular ethylene glycol and propylene glycol, and mixtures thereof, and the ethers that are derivable from the mentioned compound classes. Water-miscible solvents of this kind are preferably present in the agents in amounts no greater than 30 wt. %, in particular from 6 wt. % to 20 wt. %.

For setting a desired pH that does not result from mixing the other components themselves, the agents may contain acids that are compatible with the system and the environment, in particular citric acid, acetic acid, tartaric acid, malic acid, lactic acid, glycolic acid, succinic acid, glutaric acid, and/or adipic acid, but also mineral acids, in particular sulfuric acid, or bases, in particular ammonium or alkali hydroxides. pH regulators of this kind are optionally contained in the agents preferably in amounts no greater than 20 wt. %, in particular from 1.2 wt. % to 17 wt. %.

The production of solid agents (i.e. in particular washing or cleaning agents) poses no difficulties, and may in principle take place in a known manner, for example by spray drying or granulation, with an optional peroxygen compound and an optional bleach catalyst being optionally added later. For the production of agents having an increased bulk weight, in particular in the range of from 650 g/L to 950 g/L, a method having an extrusion step is preferred. The production of liquid agents does not pose any difficulties either, and may likewise take place in a known manner.

The preparation of the pro-fragrances is described in the examples section by way of example, with reference to the preparation of two pro-fragrances containing delta-damascones. The other pro-fragrances of general formula (I), and in particular the pro-fragrance of formulae (V) and (VI), may also be prepared via these basic synthesis routes.

According to one preferred embodiment, the teaching may be used to significantly reduce the perfume proportion in washing, cleaning and body care agents. It is thus possible to also provide perfumed products for particularly sensitive consumers who, due to specific intolerances and irritations, can use the normally perfumed products only on a limited basis or not at all.

A preferred solid, in particular powdered, washing agent, in addition to the pro-fragrance, may also contain in particular components that are selected from the following, for example:

anionic surfactants, such as preferably alkylbenzenesulfonate, alkyl sulfate, e.g. in amounts of from 5 to 30 wt. %,
 nonionic surfactants, such as preferably fatty alcohol polyglycol ether, alkyl polyglucoside, fatty acid glucamide, e.g. in amounts of preferably from 0.5 to 15 wt. %,
 builders, e.g. zeolite, polycarboxylate, sodium citrate, in amounts of e.g. from 0 to 70 wt. %, advantageously from 5 to 60 wt. %, preferably from 10 to 55 wt. %, in particular from 15 to 40 wt. %,
 alkalis, e.g. sodium carbonate, in amounts of e.g. from 0 to 35 wt. %, advantageously from 1 to 30 wt. %, preferably from 2 to 25 wt. %, in particular from 5 to 20 wt. %,
 bleaching agents, e.g. sodium perborate, sodium percarbonate, in amounts of e.g. from 0 to 30 wt. %, advantageously from 5 to 25 wt. %, preferably from 10 to 20 wt. %,
 corrosion inhibitors, e.g. sodium silicate, in amounts of e.g. from 0 to 10 wt. %, advantageously from 1 to 6 wt. %, preferably from 2 to 5 wt. %, in particular from 3 to 4 wt. %,
 stabilizers, e.g. phosphonates, advantageously from 0 to 1 wt. %,
 foam inhibitors, e.g. soap, silicone oils, paraffins, advantageously from 0 to 4 wt. %, preferably from 0.1 to 3 wt. %, in particular from 0.2 to 1 wt. %,
 enzymes, e.g. proteases, amylases, cellulases, lipases, advantageously from 0 to 2 wt. %, preferably from 0.2 to 1 wt. %, in particular from 0.3 to 0.8 wt. %,
 graying inhibitors, e.g. carboxymethylcellulose, advantageously from 0 to 1 wt. %,
 discoloration inhibitors, e.g. polyvinylpyrrolidone derivatives, preferably from 0 to 2 wt. %,
 adjusters, e.g. sodium sulfate, advantageously from 0 to 20 wt. %,
 optical brighteners, e.g. stilbene derivatives, biphenyl derivatives, advantageously from 0 to 0.4 wt. %, in particular from 0.1 to 0.3 wt. %,
 optionally further fragrances,
 optionally water,
 optionally soap,
 optionally bleach activators,
 optionally cellulose derivatives,
 optionally soil-repellent agents, in wt. %, in each case based on the overall agent.

In another preferred embodiment, the agent is present in liquid form, preferably in gel form. Preferred liquid washing or cleaning agents and cosmetics have water contents of e.g. from 10 to 95 wt. %, preferably from 20 to 80 wt. %, and in particular from 30 to 70 wt. %, based on the overall agent. In the case of liquid concentrates, the water content may also be particularly low, e.g. <30 wt. %, preferably <20 wt. %, in particular <15 wt. %, in wt. % in each case based on the overall agent. The liquid agents may also contain nonaqueous solvents.

A preferred liquid, in particular gel-form, washing agent, in addition to the pro-fragrance, may also contain in particular components that are selected from the following, for example:

anionic surfactants, such as preferably alkylbenzenesulfonate, alkyl sulfate, e.g. in amounts of from 5 to 40 wt. %,
 nonionic surfactants, such as preferably fatty alcohol polyglycol ethers, alkyl polyglucoside, fatty acid glucamide, e.g. in amounts of preferably from 0.5 to 25 wt. %,
 builders, e.g. zeolite, polycarboxylate, sodium citrate, advantageously from 0 to 15 wt. %, preferably from 0.01 to 10 wt. %, in particular from 0.1 to 5 wt. %,
 foam inhibitors, e.g. soap, silicone oils, paraffins, in amounts of e.g. from 0 to 10 wt. %, advantageously from 0.1 to 4 wt. %, preferably from 0.2 to 2 wt. %, in particular from 1 to 3 wt. %,
 enzymes, e.g. proteases, amylases, cellulases, lipases, in amounts of e.g. from 0 to 3 wt. %, advantageously from 0.1 to 2 wt. %, preferably from 0.2 to 1 wt. %, in particular from 0.3 to 0.8 wt. %,
 optical brighteners, e.g. stilbene derivatives, biphenyl derivatives, in amounts of e.g. from 0 to 1 wt. %, advantageously from 0.1 to 0.3 wt. %, in particular from 0.1 to 0.4 wt. %,
 optionally further fragrances,
 optionally stabilizers,
 water
 optionally soap, in amounts of e.g. from 0 to 25 wt. %, advantageously from 1 to 20 wt. %, preferably from 2 to 15 wt. %, in particular from 5 to 10 wt. %,
 optionally solvents (preferably alcohols), advantageously from 0 to 25 wt. %, preferably from 1 to 20 wt. %, in particular from 2 to 15 wt. %, in wt. %, in each case based on the overall agent.

A preferred liquid softener, in addition to the pro-fragrance, may also contain in particular components that are selected from the following:

cationic surfactants, such as in particular esterquats, e.g. in amounts of from 5 to 30 wt. %,
 cosurfactants, e.g. glycerol monostearate, stearic acid, fatty alcohols, fatty alcohol ethoxylates, e.g. in amounts of from 0 to 5 wt. %, preferably from 0.1 to 4 wt. %,
 emulsifiers, e.g. fatty amine ethoxylates, e.g. in amounts of from 0 to 4 wt. %, preferably from 0.1 to 3 wt. %,
 optionally further fragrances,
 dyes, preferably in the ppm range,
 stabilizers, preferably in the ppm range,
 solvents, e.g. water, in amounts of preferably from 60 to 90 wt. %, in wt. %, in each case based on the overall agent.

A further non-limiting embodiment relates to a cosmetic agent, the cosmetic agent containing a ketone of general formula (I).

A further non-limiting embodiment relates to a method for long-lastingly fragrancing surfaces, a ketone of general formula (I) or a washing or cleaning agent being applied to the surface to be fragranced (e.g. textiles, dishes, floors), and said surface is then exposed to electromagnetic radiation having a wavelength of from 200 to 600 nm.

A further non-limiting embodiment relates to a method for long-lastingly fragrancing a room, an air-care agent being exposed to electromagnetic radiation having a wavelength of from 200 to 600 nm.

EXAMPLES

Example 1: Synthesis of dodecyl-2-benzoyl-3-methyl-5-oxo-5-(2,6,6-trimethylcyclohex-3-enyl)pentanoate Stage 1: Benzoyl Acetic Acid Dodecyl Ester

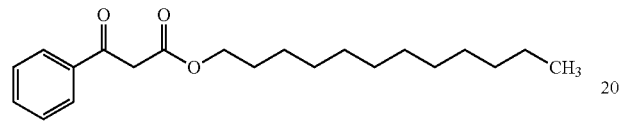

10 mmol of benzoyl acetic acid ethyl ester and 12 mmol of 1-dodecanol was provided in 30 ml of toluene in a round-bottom flask and heated for 6 hours to reflux. The solvent was distilled and the resulting product was purified by column chromotography (EtOAc:c-Hex 1:10, $R_f$=0.51); yield 97%.

Stage 2: Dodecyl-2-benzoyl-3-methyl-5-oxo-5-(2,6,6-trimethylcyclohex-3-enyl)pentanoate

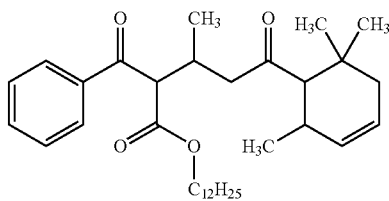

A mixture of 9 mmol of benzoyl acetic acid dodecyl ester, 9 mmol of delta-damascone and 0.9 mmol of iron(III) chloride hexahydrate was stirred into 2 ml of chloroform for 48 hours at 50° C. in a round-bottom flask. The raw product was then purified by column chromatography (MTBE:c-Hex, 1:5 $R_f$=0.68); yield 88%.

Example 2: Release Behavior

The test substance was formulated into a softener in equal molar amount compared with the odorant contained therein (corresponding to 0.4 wt. % of delta-damascone), and said softener was used in the rinsing stage of a wash process. After drying, the laundry treated in this manner was irradiated at 0.6 W/cm² for 1 minute using the sunlight simulation device Atlas Suntest XXL+. The fabric swatches were located in a Petri dish with a quartz glass cover (transparent to the entire light spectrum). After irradiation, the intensity of the fragrance was assessed by 10 people trained in odors, each sample being assessed in two independent processes, and rated on a scale of 1 to 10 (10=intense odor, 0=no odor).

Pure odorant delta-damascone was tested as a reference, in addition to the compound according to the subject matter from example 1 and AB-32 (compound from the prior art).

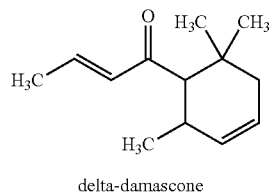

delta-damascone

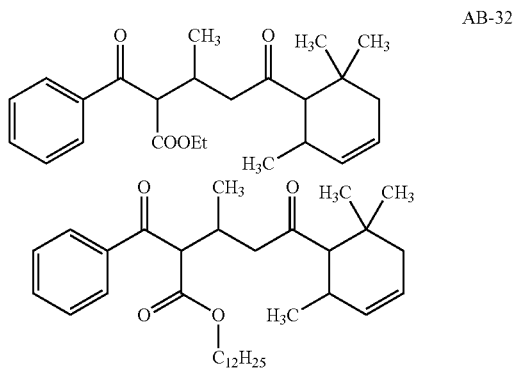

Dodecyl-2-benzoyl-3-methyl-5-oxo-5-(2,6,6-trimethylcyclohex-3-enyl)pentanoate

| Sample | Fragrance intensity after irradiation |
| --- | --- |
| Reference | 3 |
| Substance from example 1 | 6 |
| AB-32 | 4 |

It was found that the compound according to the disclosure is superior to the known substances in terms of fragrance intensity.

While the invention has been particularly shown and described with reference to specific embodiments, it should be understood by those skilled in the art that various changed in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:
1. A compound corresponding to formula (III):

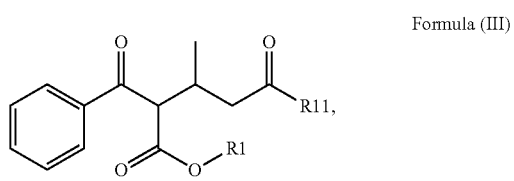

Formula (III)

wherein
R1 is a linear or branched, substituted or unsubstituted alkyl group having from 6 to 16 C atoms; and
R11 represents a hydrocarbon group having at least 5 C atoms, and having in particular a cyclic hydrocarbon group.

2. The compound according to claim 1, corresponding to one of the following formulae (IV) to (VII):

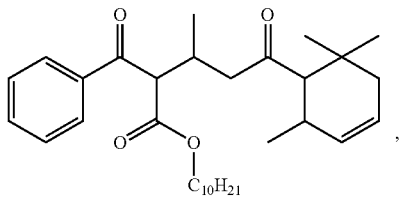
(IV)

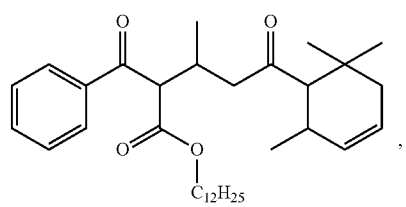
(V)

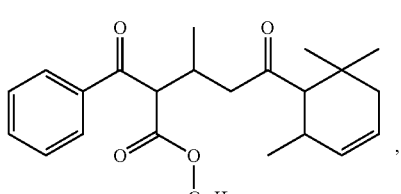
(VI)

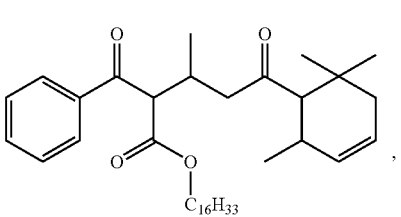
(VII)

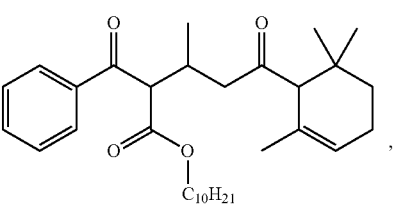
(VIII)

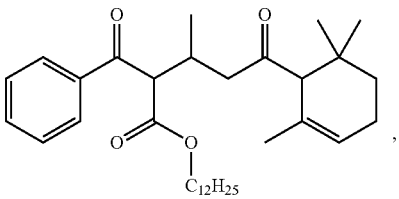
(IX)

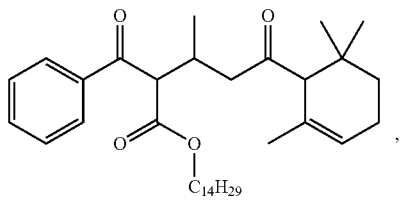
(X)

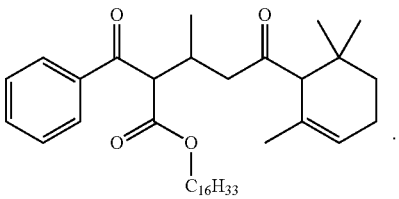
(XI)

3. A washing or cleaning agent, containing at least one compound from claim 1, wherein the compound is present in an amount ranging from 0.0001 to 5 wt. %, based on the overall agent.

4. The washing or cleaning agent according to claim 3, wherein:
(1) the cleaning agent contains at least one surfactant selected from the group consisting of an anionic surfactant, a cationic surfactant, a non-ionic surfactant, a zwitterionic surfactant, an amphoteric surfactant, and mixtures thereof; and/or
(2) the cleaning agent is present in solid or liquid form.

5. An air-care agent, containing at least one compound from claim 1, wherein the compound is present in an amount ranging from 0.0001 to 50 wt. %, based on the overall agent.

6. A cosmetic agent, containing at least one compound from claim 1, wherein the compound is present in an amount ranging from 0.0001 to 5 wt. %, based on the overall agent.

7. A method for long-lastingly fragrancing surfaces comprising:
applying at least one compound from claim 1 to a surface to be fragranced; and
exposing the surface to electromagnetic radiation having a wavelength from 200 to 600 nm.

* * * * *